(12) United States Patent
Wang et al.

(10) Patent No.: US 9,283,100 B2
(45) Date of Patent: Mar. 15, 2016

(54) POLYMER SCAFFOLD WITH MULTI-PLEATED BALLOON

(75) Inventors: Yunbing Wang, Sunnyvale, CA (US); Manish Gada, Santa Clara, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 8 days.

(21) Appl. No.: 13/473,031

(22) Filed: May 16, 2012

(65) Prior Publication Data
US 2013/0310913 A1 Nov. 21, 2013

(51) Int. Cl.
*A61F 2/84* (2006.01)
*A61F 2/958* (2013.01)
*A61F 2/915* (2013.01)
*A61M 25/10* (2013.01)
*A61F 2/95* (2013.01)

(52) U.S. Cl.
CPC .............. *A61F 2/958* (2013.01); *A61F 2/915* (2013.01); *A61F 2002/91575* (2013.01); *A61F 2002/9522* (2013.01); *A61F 2230/005* (2013.01); *A61M 25/1038* (2013.01); *Y10T 29/49908* (2015.01)

(58) Field of Classification Search
CPC ............ A61F 2/958; A61F 2002/9583; A61F 2002/9522; A61F 2002/9586
USPC ............. 623/1.11; 604/509; 29/505; 264/239
See application file for complete search history.

(56) References Cited

U.S. PATENT DOCUMENTS

| 4,994,072 | A | 2/1991 | Bhate et al. |
|---|---|---|---|
| 5,087,246 | A | 2/1992 | Smith |
| 5,556,383 | A | 9/1996 | Wang et al. |
| 5,693,014 | A | 12/1997 | Abele et al. |
| 6,488,688 | B2 | 12/2002 | Lim et al. |
| 6,629,350 | B2 | 10/2003 | Motsenbocker |
| 6,666,880 | B1 | 12/2003 | Chiu et al. |
| 6,942,681 | B2 | 9/2005 | Johnson |
| 7,010,850 | B2 | 3/2006 | Hijlkema et al. |
| 7,316,148 | B2 | 1/2008 | Asmus et al. |
| 8,046,897 | B2 | 11/2011 | Wang et al. |
| 8,123,793 | B2 | 2/2012 | Roach et al. |
| 2003/0055482 | A1* | 3/2003 | Schwager et al. ........... 623/1.11 |
| 2005/0143752 | A1 | 6/2005 | Schwager et al. |
| 2005/0244533 | A1 | 11/2005 | Motsenbocker et al. |
| 2006/0076708 | A1* | 4/2006 | Huang et al. .................. 264/239 |
| 2007/0289117 | A1 | 12/2007 | Huang et al. |
| 2008/0114331 | A1* | 5/2008 | Holman et al. ............... 604/509 |

(Continued)

FOREIGN PATENT DOCUMENTS

| DE | 198 33 501 | 1/2000 |
|---|---|---|
| EP | 2 147 695 | 1/2010 |
| WO | WO 2012/145326 | 10/2012 |

OTHER PUBLICATIONS

U.S. Appl. No. 13/089,225, filed Apr. 18, 2011, Roberts et al.
U.S. Appl. No. 13/194,162, filed Jul. 29, 2011, Stankus et al.
International Search Report and Written Opinion for PCT/US2013/040535, mailed Aug. 13, 2013, 11 pgs.

(Continued)

*Primary Examiner* — Thomas McEvoy
*Assistant Examiner* — Julie A Szpira
(74) *Attorney, Agent, or Firm* — Squire Patton Boggs (US) LLP

(57) ABSTRACT

A medical device includes a polymer scaffold crimped to a balloon. The balloon is formed with between 6 and 15 pleats to provide a uniform expansion of the scaffold when the balloon is inflated. Also provided are methods for crimping a scaffold to a multi-pleated balloon and methods for making a multi-pleated balloon.

17 Claims, 8 Drawing Sheets

(56) References Cited

U.S. PATENT DOCUMENTS

| | | |
|---|---|---|
| 2008/0275537 A1 | 11/2008 | Limon |
| 2009/0001633 A1 | 1/2009 | Limon et al. |
| 2010/0004735 A1 | 1/2010 | Yang et al. |
| 2010/0025894 A1 | 2/2010 | Kleiner et al. |
| 2010/0063571 A1* | 3/2010 | Roach et al. .................. 623/1.11 |
| 2011/0270383 A1 | 11/2011 | Jow et al. |
| 2012/0079706 A1 | 4/2012 | Knott et al. |

OTHER PUBLICATIONS

Bosiers et al., "Coronary and endovascular applications of the Absorb™ bioresorbable vascular scaffold", Interv. Cardiol. 4(6), pp. 621-631 (2012).

Miller "Abbott's Bioresorbable Stent Shows Durable Results in ABSORB Trial", The Gray Sheet, pp. 17-18, Mar. 2003.

* cited by examiner

POLYMER SCAFFOLD WITH MULTI-PLEATED BALLOON

BACKGROUND OF THE INVENTION

1. Field of the Invention

The present invention relates to drug-eluting medical devices; more particularly, this invention relates to processes for crimping a polymeric scaffold to a delivery balloon.

2. Background of the Invention

The art recognizes a variety of factors that affect a polymeric scaffold's ability to retain its structural integrity when subjected to external loadings, such as crimping and balloon expansion forces. According to the art, characteristics differentiating a polymeric, bio-absorbable scaffolding of the type expanded to a deployed state by plastic deformation from a similarly functioning metal stent are many and significant. Indeed, several of the accepted analytic or empirical methods/ models used to predict the behavior of metallic stents tend to be unreliable, if not inappropriate, as methods/models for reliably and consistently predicting the highly non-linear behavior of a polymeric load-bearing portion of a balloon-expandable scaffold (hereinafter "scaffold"). The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA"), and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

One challenge to a polymeric scaffold is crimping to a balloon and expansion of the scaffold when the balloon is inflated. Problems arise where, on the one hand, the scaffold cannot be crimped to the desired size without introducing structural failure, i.e., fracture, or excessive cracking, either in the crimped state or when expanded from the crimped state by a balloon. On the other hand, a scaffold can be crimped and deployed, yet deploys with non-uniformity in its deployed state. In these cases the scaffold is susceptible to acute or fatigue failure as the irregularly-deployed rings and/or cells, loaded beyond their design limits as a consequence of the non-uniform deployment, have a reduced acute or fatigue life within the vessel.

Additionally, the retention force keeping a crimped scaffold on a delivery balloon during transit through tortuous anatomy is sometimes not sufficiently high to preclude premature dislodgment of the scaffold from the balloon. If the scaffold is not held on the balloon with sufficient force, e.g., as where there is recoil in the scaffold following crimping or the coefficient of friction between balloon and scaffold is too low, the scaffold can become separated from the balloon as the catheter distal end flexes and/or impinges on walls of the delivery sheath. For a metallic stent, there are several well-known approaches for increasing the retention of the stent to a balloon during transit to the target site. However, methods proposed thus far for retaining the scaffold on a balloon are in need of improvement, or inappropriate for a polymer scaffold.

In one example of a method for crimping a metallic stent to a delivery balloon, the stent is placed in a crimper and the temperature elevated to facilitate greater compliance in the balloon material to allow material to extend between gaps in the stent struts. Additionally, balloon pressure is maintained while the stent is being crimped to increase stent retention to the balloon. After an initial pre-crimp, the stent is placed on the delivery balloon and allowed to slightly recoil under balloon pressure and while the stent has an elevated temperature. After this step, the stent is crimped onto the balloon while the balloon is pressurized. The stent is cycled through larger and smaller diameters. Additionally, balloon pressure may be supplied in bursts or held constant during these crimping steps. Further details of this process may be found in U.S. application Ser. No. 12/895,646 filed Sep. 30, 2010.

The art previously devised methods for retaining a balloon-expanded polymer scaffold on a delivery balloon. In one example, the scaffold is crimped to the delivery balloon at a temperature well below the polymer's TG. Then the scaffold, disposed between ends of the balloon, is thermally insulated from the balloon's ends. The ends of the balloon are then heated to about 185 degrees Fahrenheit to expand the diameter of the balloon material at its ends. The expanded balloon ends form raised edges abutting the scaffold ends to resist dislodgment of the scaffold from the balloon. In one example, this process provided a retention force of about 0.35 lb. for a Poly (L-lactide) (PLLA) scaffold crimped to a polymide-polyether block co-polymer (PEBAX) balloon. An example of this process is disclosed in U.S. Pat. No. 6,666,880.

Another example of a polymer scaffold crimping is found in U.S. Pat. No. 8,046,897, which has a common inventor with the present application. The balloon is inflated, or partially inflated before crimping. The scaffold is placed on the balloon. The crimping may take place at elevated temperatures, e.g., 30-50 degrees Celsius.

There is a continuing need to improve upon methods for crimping a polymer scaffold to a delivery balloon in order to improve upon the uniformity of deployment of a polymer scaffold from the balloon.

SUMMARY OF THE INVENTION

The invention provides methods for increasing uniformity of polymer scaffold expansion via a balloon-inflation delivery system. A preferred use for the invention is crimping a polymer scaffold to a delivery balloon having an increased number of pleats formed thereon.

It has been found that certain modifications to processes and products related to crimping and balloon expansion of a polymer scaffold can be made to improve-upon a need for increasing the uniformity of polymer scaffold expansion from a delivery balloon. According to the invention, a balloon having a greater number of pleats can satisfy or improve upon this need.

In one aspect a polymer scaffold is crimped to a balloon having at least 6 pre-made pleats, or between 9 and 15 pre-made pleats. The scaffold crimping process may inflate the balloon after the scaffold has been partially crimped, or the balloon may remain un-inflated throughout the crimping process. According to the former process, balloon inflation may be included during the crimping process to increase the balloon-scaffold retention. Preferably, the balloon expansion is initiated after the scaffold diameter has been reduced by an amount that prevents the pleats in the balloon from fully unfolding, e.g., at least about 50% reduction from a pre-crimp diameter. In this way, the increased uniformity of expansion provided by a multi-pleated balloon is retained while, at the same, scaffold-balloon retention may be increased.

The number of pleats chosen for the balloon may be related to the scaffold pattern, since the scaffold pattern (i.e., numbers of linking elements, crowns, closed cells, etc.) informs one of the space available for balloon material in relation to the circumferential extent of a pleat, and contribution to the overall radial force imposed on the scaffold by an individual pleat. In each case, the objective is to increase the number of pre-made folds or pleats opposing gaps between struts. For instance, at least 2N or 3N pleats for N linking elements between a pair of rings
at least one pleat for every crown in a ring
at least 3 pleats for every closed cell In a preferred embodiment 12 pleats are chosen. The number of pleats may be 6, 9, 12 or 15, between 9 and 15, or between 12 and 15.

According to another aspect of the invention, a medical device includes a polymer scaffold crimped to a balloon, the scaffold having a longitudinal axis and ring elements, wherein a pair of ring elements are connected to each other by at least 2 linking elements; wherein the balloon is formed to have at least 6 pleats so as to cause the scaffold to expand uniformly when the balloon is inflated. The scaffold may be formed from a semi-crystalline polymer tube that is bi-axially expanded to have a pre-crimp diameter that is at least twice the diameter of the scaffold when crimped to the balloon, such that the scaffold having the crimped diameter has a polymer chain orientation resulting from the biaxial expansion of the tube. The balloon has a longitudinal axis and the pleats may extend over the longitudinal axis. The pleats may be heat set pleats and wrapped in spiral fashion about the balloon.

According to another aspect of the invention, a method for making medical device includes the steps of providing a polymer scaffold having a longitudinal axis, pre-crimp diameter and a pair of ring elements connected to each other by at least two linking elements; providing a balloon formed with at least six pleats; and crimping the scaffold to the balloon, including reducing the scaffold diameter from the pre-crimp diameter to a first diameter, maintaining the scaffold at the first diameter for a dwell period, and reducing the scaffold diameter from the first diameter to a final crimp diameter. The balloon may be inflated after the scaffold has attained the first diameter.

According to another aspect of the invention, there is a method for making a multi-pleated balloon using a mold cavity having at least 6 radially extending slots for forming balloon pleats and a circular portion for radially expanding an extruded tube of polymer material. The method includes the steps of extruding the tube and disposing the tube within the mold cavity, radially expanding the tube at a first pressure, and when the expanded tube reaches a slot, increasing the pressure to a second pressure to cause the polymer material to extend into the slots, thereby forming the pleats.

According to another aspect of the invention, there is a method for making a multi-pleated balloon using a polymer material using a forming chamber having at least 6 openings and corresponding radially extending fingers configured for being extended radially inward from the openings to form pleats in a balloon disposed within the chamber. The method includes the steps of forming a balloon, placing the balloon within the chamber, lightly pressuring the balloon, then radially extending the fingers into the balloon to form the pleats.

In a preferred embodiment a crimping process includes an alignment check. The balloon inflated state is preferably maintained during the alignment check. In other embodiments one may dispense with the alignment check, so that the scaffold is removed from the crimper only after it is fully crimped to the balloon.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 1A shows the arrangement of balloon material when the balloon is not inflated during crimping. FIG. 1B shows the arrangement of balloon folds when the balloon is partially inflated during crimping.

DETAILED DESCRIPTION OF EMBODIMENTS

Figure 1A:
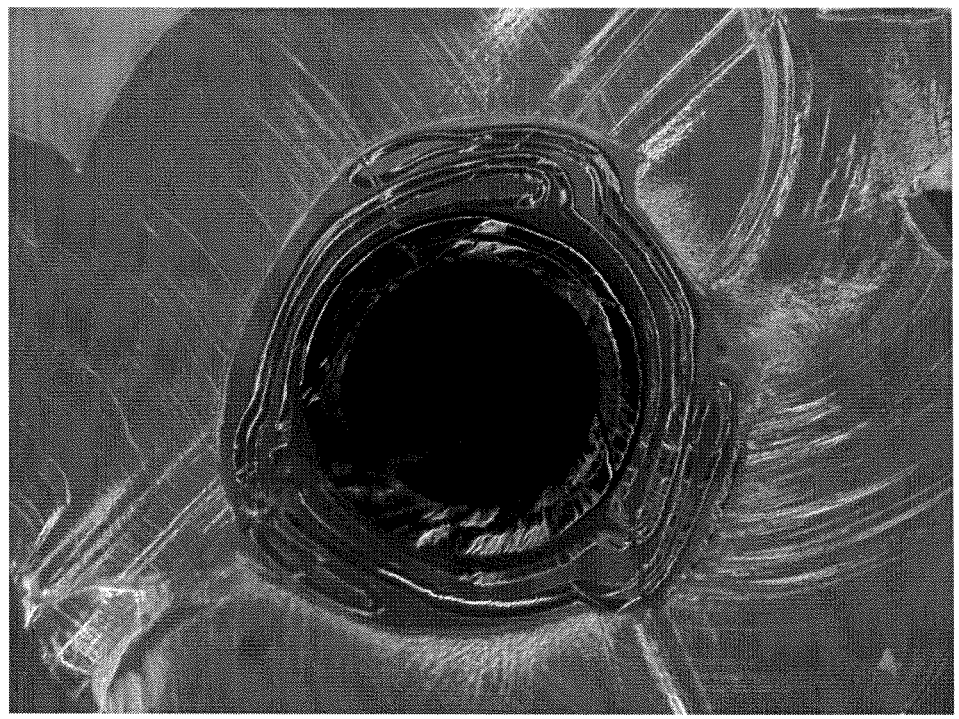
FIGS. 1A and 1B shows arrangements of balloon material about a catheter shaft after completion of crimping processes using a balloon having three pleats.

The "glass transition temperature," TG, is the temperature at which the amorphous domains of a polymer generally change from a brittle, vitreous state to a solid deformable or ductile state at atmospheric pressure, as discussed in greater detail in US 2010/0004735.

Poly(lactide-co-glycolide) (PLGA) and Poly (L-lactide) (PLLA) are examples of a class of semi-crystalline polymers that may be used to form the scaffolds crimped to multi-pleated balloons according to the disclosure. PLLA is a homopolymer and PLGA is a co-polymer. The percentage of glycolide (GA) in a scaffold constructed of PLGA may vary, which can influence the lower range of TG. For example, the percentage of GA in the matrix material may vary between 0-15%. For PLLA, the onset of glass transition occurs at about 55 degrees Celsius. With an increase of GA from about 0% to 15% the lower range for TG for PLGA can be correspondingly lower by about 5 degrees Celsius. For PLGA having % GA of about 5% the temperature ranges for crimping may be between about 46 to 53 degrees Celsius. For PLGA having % GA of about 15% the temperature ranges for crimping are about 43 to 50 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in U.S. Pub. No. 2010/00025894.

A scaffold's outer diameter (made according to the foregoing processes) may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to over-extend the scaffold to ensure it stays in place. For this reason, it is sometimes preferred to use a tube with a diameter larger than the expected deployed diameter of the scaffold.

As discussed earlier, fabrication of a scaffold presents challenges that are not present in metallic stents. One challenge, in particular, is the fabrication of a scaffold, which means the load bearing network of struts including connectors linking ring elements or members that provide the radial strength and stiffness needed to support a lumen. In particular, there exists a need to fabricate a scaffold capable of undergoing a significant degree of plastic deformation without loss of strength, e.g., cracks or fracture of struts. In one embodiment the ratio of deployed to fully crimped diameter is about 2.5. In this embodiment, the crimped diameter corresponds to an outer diameter that is only about 40% of the starting diameter. Hence, when deployed the drug eluting scaffold is expected to increase in size at least to about 2.5 times its crimped diameter size.

In one particular example, a scaffold is formed from a bi-axially expanded tube having an outer diameter of 3.5 mm, which approximately corresponds to a deployed diameter (the scaffold may be safely expanded up to 4.0 mm within a lumen). The iris of the crimping mechanism reaches a diameter of 0.044 in, which is maintained for a 185 sec dwell period (i.e., scaffold held at 0.044 in outer diameter within crimping mechanism). When later removed from the crimper, the scaffold will recoil despite there being a restraining sheath placed over the scaffold immediately after the scaffold is removed from the crimper. The scaffold and sheath are then subjected to radiation sterilization. At the point of use, i.e., at the point in time when a medical specialist removes the restraining sheath, the scaffold has an outer diameter of about 0.052 in (1.32 mm), or about 35-40% of the starting tube diameter of 3.5 mm. When in the crimping mechanism the scaffold reaches about 30-35% of the starting tube size.

The above range of plastic deformation of the scaffold in this example requires a carefully chosen crimping process, which take into account the visco-elastic nature of the material and need for allowing a sufficient degree of mobility of polymer chains within the material so that the material does not crack. See US20110270383 which is co-owned with the present application.

Similar concerns for a scaffold's structural integrity can arise when the scaffold is delivered to a vessel location and expanded by the balloon. It is desirable that the scaffold be deployed uniformly. If expanded non-uniformly crowns or other high strain regions of the scaffold can experience excessive strain that can weaken the structure. According to one aspect of the disclosure, a multi-pleated balloon, e.g., 12 pleats, is proposed as a delivery balloon for a polymer scaffold to improve the uniformity of expansion of the crimped scaffold within the vessel.

A balloon according to the disclosure is formed to have pleats or wings that open when pressure is supplied to the balloon. Processes of a forming such wings or pleats or folds (hereinafter "folds") is a common practice for semi- or non-compliant balloon. Examples of these types of balloons are described in U.S. Pat. No. 5,556,383, U.S. Pat. No. 6,488,688 and U.S. Pub. No. 2005/0244533. The pleats are formed by folds made in the balloon. The balloon material is folded according to a particular pattern or design intended to achieve an objective, e.g., a minimum profile. The folding is undertaken in an orderly manner either by hand or by a machine process, e.g., U.S. Pub. No. 2005/0244533. The balloon is typically heat set to hold the pleats in place, thereby forming pre-made or pre-set pleats.

For non-compliant balloons, which use material that is essentially non-elastic within the balloon operating ranges, the balloon inflates when pleats have unfolded. As such, non-compliant balloons sometimes have several tightly wound layers of prearranged folded balloon material when in the collapsed configuration in order to achieve a minimum profile or diameter for the balloon. Balloon pleats may be folded in a spiral or accordion like fashion, each approach to achieve a specific objective, e.g., low profile or reduced manufacturing complexity or quality control. Once folded, the balloon is heat set so that the balloon pleats are maintained in a tightly wound configuration about a catheter shaft. The heat set can be such that if the balloon pressure is increased enough to unfold the pleats, and then the balloon pressure is reduced back to, or below atmospheric; the balloon will take the same shape as it had prior to inflation. Above a certain inflation amount, the pleats can become completely or partially undone (so that when the inflation pressure is removed the folds do not return to their original heat-set pattern) as a scaffold interferes with the partially opened pleats. Such a situation occurs when the balloon is inflated during crimping or after a partial crimping of a scaffold to the balloon.

Metal stents have traditionally used expansion balloons having 2 or 3 pleats to expand the metal stent to an expanded state. There has also been some use of these same types of balloons to radially expand crimped polymer scaffold. In the case of metal stents, the unfolding behavior of the balloon has been generally found acceptable with respect to the resulting structural integrity of the metal stent after deployment. There are instances of non-uniform expansion of a metal stent resulting from a pleated balloon's asymmetric inflation sequence, but this non-uniformity has not typically affected the strength properties of the structure. However, the same is not true for a crystalline, or semi-crystalline polymer scaffold, which is far less ductile than a metal.

Figure 1B:
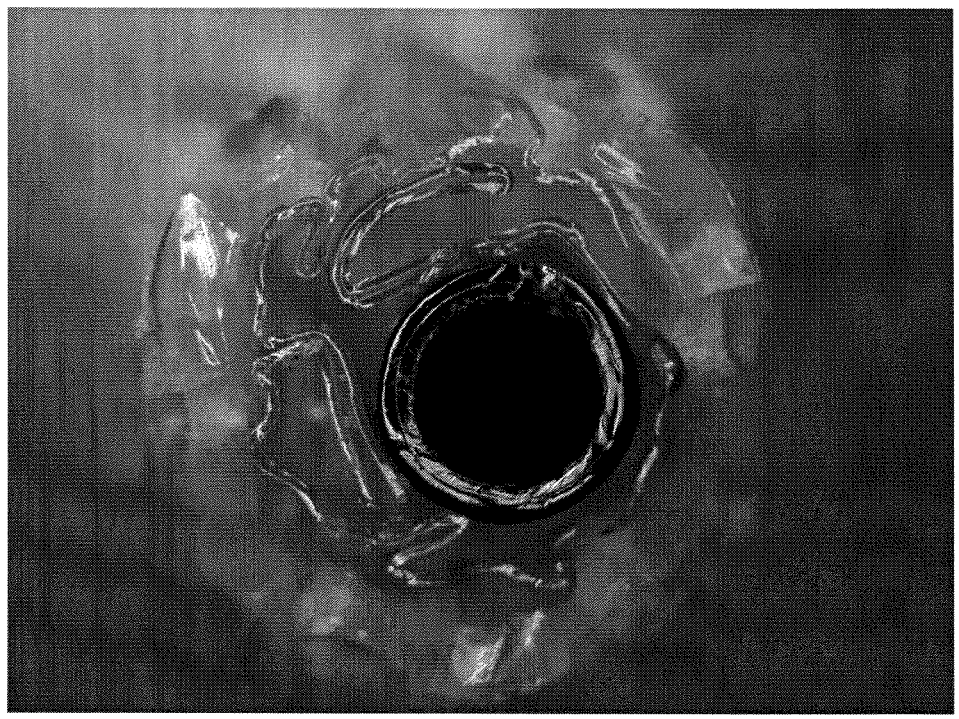

FIGS. 1A and 1B are photographs showing the cross-sections of a scaffold crimped to a balloon having three pleats. FIG. 1A shows the arrangement of balloon folds after crimping the scaffold to the balloon without inflating the balloon during the crimp process. As can be seen, the balloon material more or less retains the heat-set folds typical for a balloon having three pleats. FIG. 1B shows the arrangement of balloon folds after the scaffold was crimped to the balloon where the balloon is partially inflated during the crimping process (the balloon is inflated to increase balloon-scaffold retention, as discussed infra). The inventors found that in the case of FIG. 1A or 1B the balloon inflation sequence is not symmetric as the pleats do not open simultaneously. As a result, the balloon imposes a varying outward radial force on the scaffold when expanded.

Figure 2:
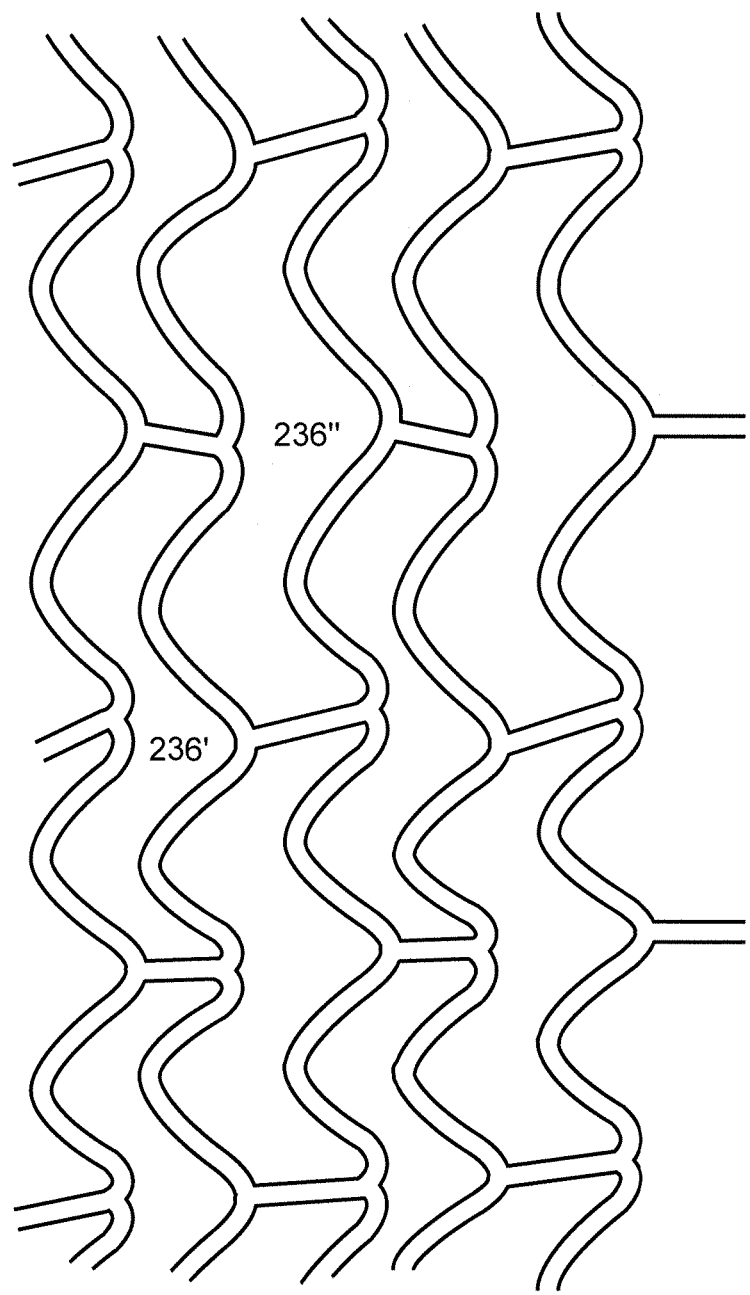
FIG. 2 shows a portion of a scaffold after balloon expansion for a scaffold crimped using the three-pleated balloon.

FIG. 2 depicts a portion of a scaffold after being non-uniformly expanded by a balloon. The shapes of the cell regions, e.g., 236' and 236", are irregular. These irregular-shaped cells indicate that some rings have been expanded beyond their design angles while others have not been expanded to their design angles. The over-extended angles can lead to crack propagation at the crown and in some cases, failure of rings at or near the crown. While the net result is the intended expanded diameter, e.g., about 3.5 mm, the distribution of stresses among the ring struts is uneven and affects the structural integrity of the expanded scaffold.

The cause of the non-uniformity, as mentioned above, is the asymmetric or sequential nature of how a pleated balloon may unfold. Although the intent, when forming and wrapping pleats is to have each of the three pleats simultaneously fill with fluid when an inflation pressure is supplied, it is common that one pleat will open more, or at a greater rate than other pleats (e.g., as a result of one or two of the pleats being pressed-in more during the heat-set or wrapping process, with the result that the third pleat opens more quickly or inflates faster since the fluid passageway into this pleat opens more quickly than the others). In any case, one cannot expect that each pleat of a balloon will open simultaneously to produce everywhere equal radial-outward forces on the scaffold.

To address this asymmetry, the inventors propose increasing the number of pleats in the balloon. With a greater number of pleats, it is believed that any non-uniformity in scaffold expansion can be reduced, either because less balloon material presses down on other pleats, or the effect of one pleat expanding before others will have less effect on the net radial force imposed on the scaffold. The discovery was made based on inspection of balloon material for scaffolds crimped to a balloon that were fully inflated prior to crimping the scaffold to the balloon. The expanded scaffolds exhibited a marked improvement in uniformity of expansion. When the arrangement of balloon material beneath this scaffold was inspected, it was found that several evenly distributed folds where present. From this observation it was concluded that a balloon having a greater number of pleats could produce a similar result.

A multi-pleated balloon according to the disclosure may have between 6 and 15, or 9 and 15, or 12 and 15 pleats. The balloon may remain un-inflated during a crimping process or the balloon may be inflated during the crimping process to increase scaffold-balloon retention. Moreover, the number of pleats for the balloon may be related to the scaffold pattern, e.g., the number of linking elements connecting rings.

Figure 5A:
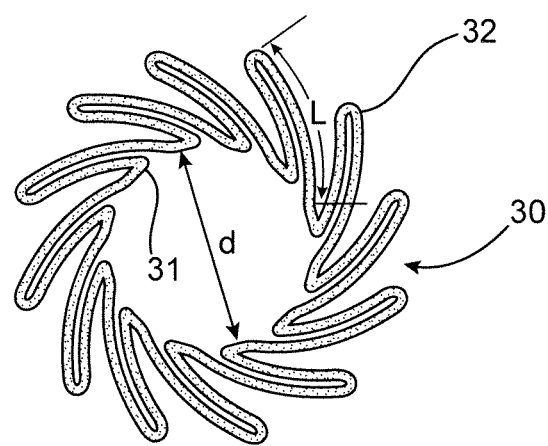
FIG. 5A shows a cross-sectional view of a twelve-pleated balloon. The pleats are shown partially wrapped around a hub of the balloon in spiral fashion.
Figure 5B:
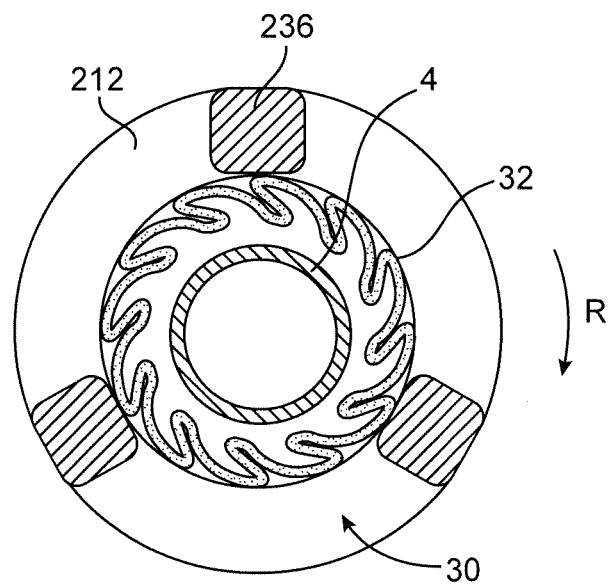
FIG. 5B shows a cross-sectional view of a scaffold partially crimped to the twelve-pleated balloon of FIG. 5A with the balloon partially inflated and pleats partially opened.

FIGS. 5A and 5B illustrate aspects of a six-pleat balloon 20 according to the disclosure. FIG. 5A shows a cross-sectional view of the balloon 20 in the non-inflated state with each of the six pleats 22 partially wrapped in a spiral fashion around the hub 21 of the balloon 20. FIG. 5B shows a cross-sectional view of a partially crimped scaffold over the partially expanded six-pleat balloon 20 when the scaffold is being crimped within a crimper head. The scaffold is shown in a partially crimped state, e.g. its diameter is reduced to about ½ of its pre-crimp diameter within the crimper head, so that the balloon can be only partially expanded and pleats substantially or partially retain their shape. This scaffold has rings 212 connected by three linking elements 236, e.g., the scaffold depicted in FIG. 3. Thus, for a medical device with a scaffold pattern as shown in FIG. 3 crimped to the six-pleat balloon 20, there are two pleats for every cell formed by adjacent rings, or two pleats for every linking element.

Figure 6A:
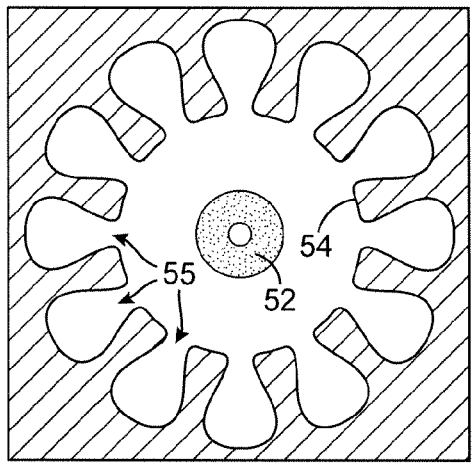
FIGS. 6A-6C illustrate a process for making a multi-pleated balloon. Shown is a mold cavity for radially expanding an extruded tube. The cavity includes radially outward extending slots for forming pleats.
Figure 6B:
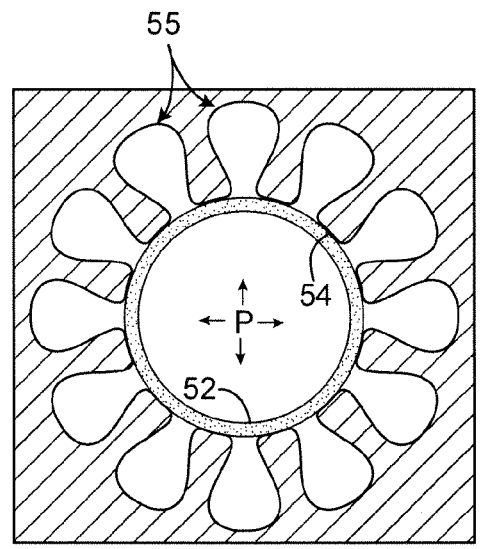

FIGS. 6A and 6B illustrate aspects of a twelve-pleated balloon 30 according to the disclosure. FIG. 6A shows a cross-sectional view of the balloon 30 in the non-inflated state with each of the twelve pleats 32 partially wrapped in spiral fashion about the balloon hub 31. FIG. 6B shows a cross-sectional view of the partially crimped scaffold from FIG. 5B over the partially expanded twelve-pleated balloon 30 when the scaffold is being crimped within a crimper head. Thus, for a medical device with a scaffold pattern as shown in FIG. 3 crimped to the twelve-pleat balloon of FIG. 6B, there are four pleats for every cell formed by adjacent rings, or four pleats for every linking element.

Figure 3:
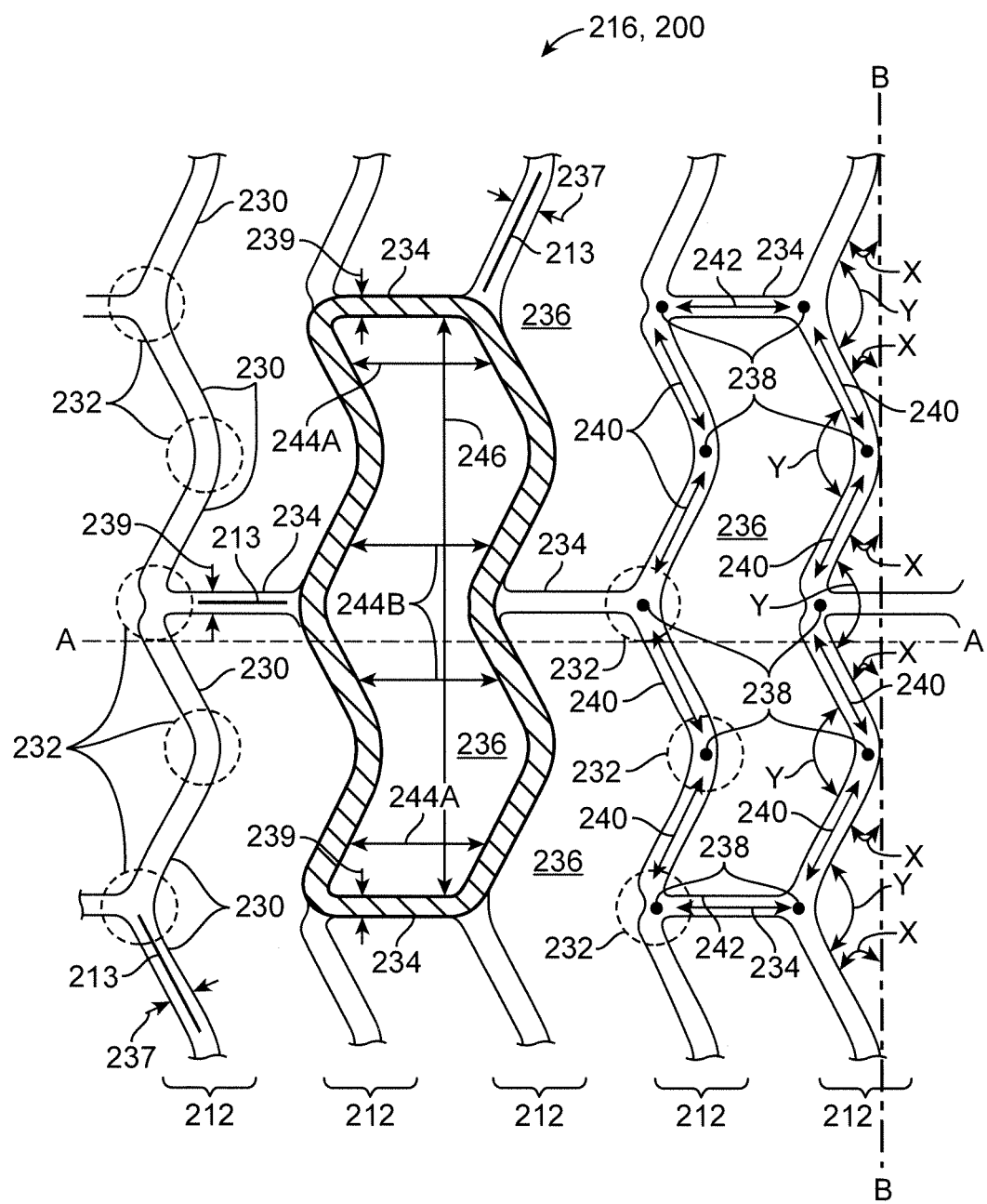
FIG. 3 shows an example of a portion of a scaffold for crimping to, and expanding from a multi-pleat balloon according to the disclosure.

In another aspect of the disclosure, it is contemplated that for a polymer scaffold having N linking elements, e.g., N=3 linking elements 236 for the scaffold of FIG. 3, a balloon having at least 2N, 3N, N4 or 5N pleats can provide a sufficient number of pleats between links to reduce the effect of irregular expansion of pleats contributing varying radial forces on the scaffold. It is contemplated that by increasing the number of pleats per linking element, the effects on the scaffold structure resulting from a pleat expanding before others have expanded will be reduced. In essence, the outward force on the scaffold structure by an individual pleat will be smaller in comparison to the net radial outward force since the pleat comes in contact with less of the scaffold structure or the pressure applied to the scaffold is a smaller percentage of the overall radial outward force causing the scaffold to expand.

According to another aspect of the disclosure, there are crimping processes for multi-pleated balloons according to the disclosure. As mentioned earlier, a crimping process using a multi-pleated balloon may or may not include inflation of the balloon after the scaffold has been partially crimped. When an increase in the scaffold-balloon retention force is needed, the balloon may be inflated as this encourages more balloon material to extend between struts when the scaffold is being crimped to the balloon.

Crimping Methods

A "retention force" for a scaffold crimped to a balloon means the maximum force applied to the scaffold along the direction of travel through a vessel that the scaffold-balloon is able to resist before dislodging the scaffold from the balloon. The retention force for a scaffold on a balloon is set by a crimping process, whereby the scaffold is plastically deformed onto the balloon surface to form a fit that resists dislodgment of the scaffold from the balloon. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. As such, the magnitude of a pull off or retention force for a scaffold generally varies with its length. The shorter scaffold, therefore, is more likely to dislodge from the balloon as the catheter is pushed through tortuous anatomy than a longer scaffold where the same crimping process is used for both the longer and shorter scaffolds.

Previous approaches for improving scaffold retention to a balloon have been proposed. For example, U.S. patent application Ser. No. 12/772,116 filed Apr. 30, 2010 (US20110270383) ('116 application) discusses a study that was conducted to investigate the effects on retention forces for crimped scaffolds for different temperature ranges. Principally, this study identified a temperature range relative to a TG of the scaffold material that improved retention forces without detrimentally affecting scaffold mechanical properties when deployed to support a vessel. For PLLA it was found that modifying the pressure and hold time of the scaffold for crimping temperatures of between about 40° and 55° C. improved the scaffold retention, with about 45-51° C. and about 48° C. being preferred temperatures for a PLLA scaffold. Additionally, the '116 application found that retention forces could be improved if the scaffold were crimped down to an intermediate diameter and then the balloon is deflated then re-inflated, followed by crimping the scaffold down to a final crimp diameter. The '116 application also contemplates similar results for PLGA, if TG for this material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

Processes have been previously proposed for achieving a high retention force while maintaining the structural integrity of a crimped polymer scaffold. One such process is described in co-pending application Ser. No. 13/089,225 (the '225 application) having a common assignee as this application. According to this disclosure, methods are proposed that increase the retention force on an 18 mm length, 3.5 mm pre-crimp diameter scaffold by at least 0.5 lbs over the process used to produce the data in the '116 application. Unlike earlier crimping steps, the balloon is pressurized when the scaffold is crimped to the final diameter. The presence of balloon pressure during the final crimp (the "intermediate pressure" step), as compared to the same process without the "intermediate pressure" step, i.e., about atmospheric balloon pressure for the final crimp, greatly increased the retention force of the scaffold to the balloon. Stated differently, the retention force of scaffold to balloon was much higher when the balloon is pressurized during the final crimp, or diameter reduction step.

It is believed that the greatly increased retention force was achieved because the balloon material opposing gaps in scaffold struts during the final crimp tended to extend in-between gaps more often as the scaffold was crimped due to the opposing balloon pressure applied to the balloon material. Without this pressure, the balloon material tended to deflect away from the gaps as the size of the gaps narrowed during the final crimp. Essentially, the balloon pressure forced more balloon material into gaps—rather than deflect the material away from the gaps—when the diameter is being reduced in size.

Examples of a crimping process using a multi-pleated balloon are now provided.

EXAMPLE 1

Figure 8:
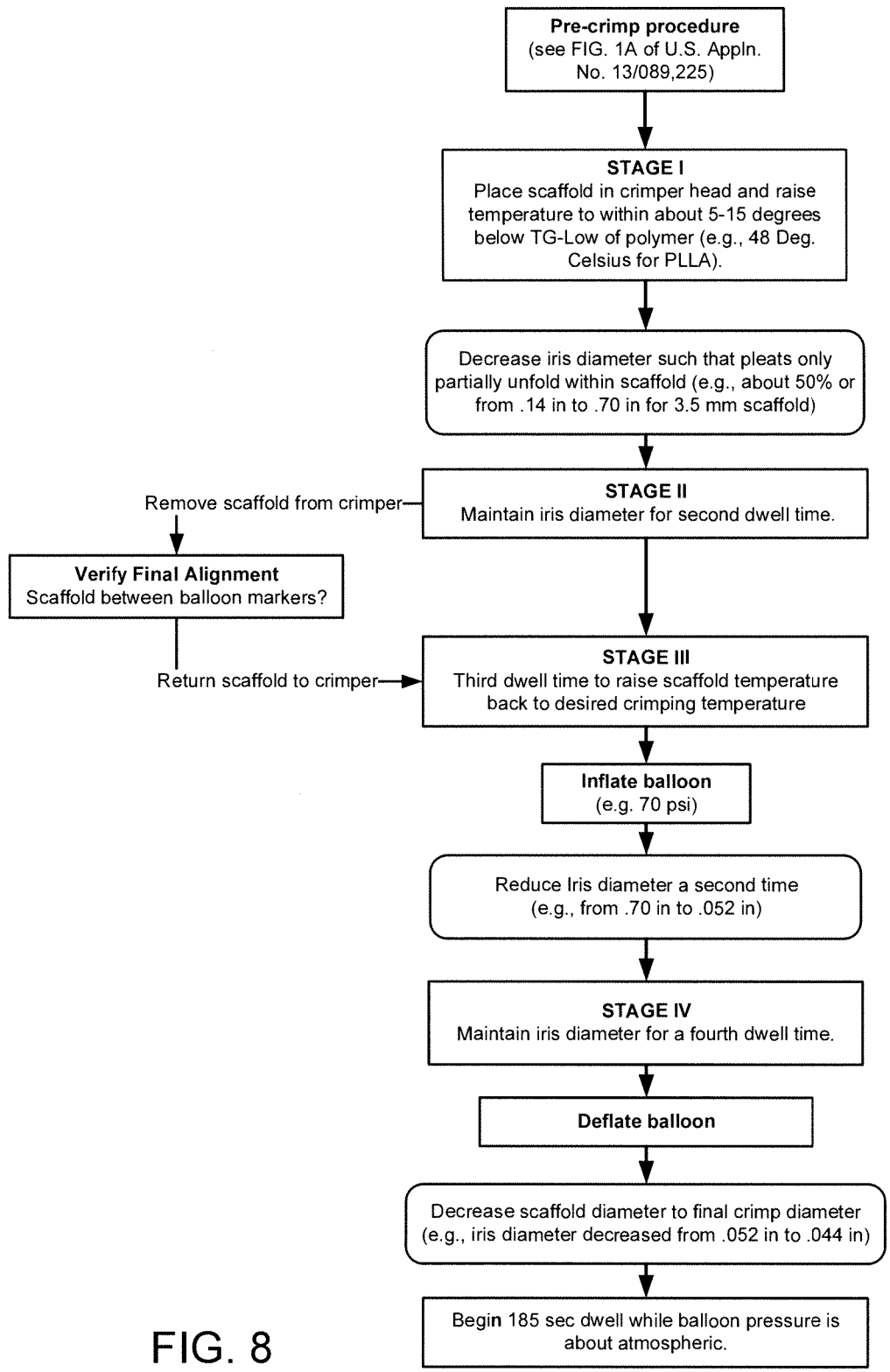
FIG. 8 is an example of a flow process for crimping a polymer scaffold to a multi-pleated balloon according to the disclosure.

FIG. 8 illustrates the steps associated with a first example of a crimping process for a 3.5 mm (0.14 in) scaffold crimped to a multi-pleated balloon according to the disclosure. Before initiating crimping, a pre-crimp procedure is implemented as described in co-pending application Ser. No. 13/089,225 co-owned with this application.

Stage I of the process places the scaffold in the crimper head and performs a dwell (iris fixed) for time period sufficient to stabilize the temperature of the scaffold at or near to the crimping temperature of less than a TG-low for the polymer. The crimper iris is then decreased until the diameter arrives at a designated diameter, which in this example is 0.7 in. The iris is then maintained at 0.7 in for a dwell period.

The scaffold is removed from the crimper head to perform an alignment check, then placed back in the crimper and dwelled sufficiently to raise the temperature of the scaffold back to about the crimper temperature. The scaffold is then crimped down to the final crimp diameter followed by another dwell period. The scaffold is removed from the crimper and immediately placed in a restraining sheath to limit recoil.

In FIG. 8 the process further includes inflating the multi-pleated balloon after the alignment check, the scaffold diameter has been reduced by at least about 50% or the scaffold diameter is reduced such that the pleats will retain essentially their pre-set shape when the balloon is inflated within the partially-crimped scaffold (the scaffold walls block or interfere with the pleats, thereby restricting their deployment).

It is not necessary that the balloon is inflated when crimping. Balloon inflation may be desired to increase scaffold retention but in some instances it may not be necessary to perform this additional step at all, or only during, or near to a final crimp step, e.g., as in the case of U.S. application Ser. No. 13/194,162, where the scaffold need not navigate tortuous passages to arrive at the target site, or the scaffold is very long.

Method of Manufacture

Figure 6C:
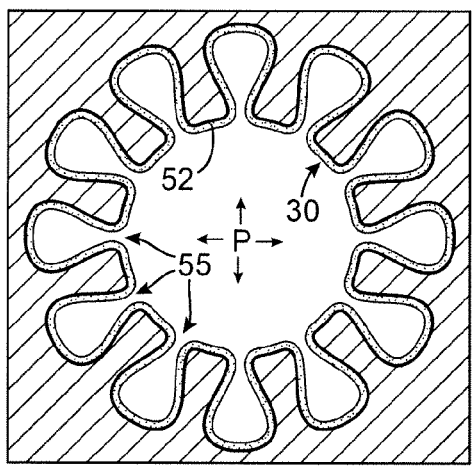

According to another aspect of the disclosure, there are methods of making a balloon having multiple pleats, i.e., between 6 and 15 pleats. FIGS. 6A-6C illustrate a first disclosure of a process for making a balloon using a mold cavity having slots arranged about the inner surface of the mold cavity for forming pleats when an extruded tube is radially expanded within the mold cavity. Illustrated in FIG. 6A-6C is a mold 50 used to make a twelve-pleat balloon by providing twelve slots or passageways extending radially outward from the inner walls of the mold cavity. Alternatively, the mold may have 6, 9, or 15 radially extending slots for making a balloon with 6, 9, or 15 pleat balloon, respectively.

A co-polymer starting tube, e.g., polymide-polyether block co-polymer (PEBAX), is formed by extrusion of the co-polymer material. The extruded, hollow tube 52 is disposed in the mold cavity 50. The extruded tube 52 is maintained at a temperature well above the higher-Tg of the co-polymer material (e.g., about 175 deg. Celsius for PEBAX) and the tube 52 is radially expanded in the mold to a larger diameter by a supplied internal pressure inside the tube 52. FIG. 6A shows the tube before supplying this internal pressure (P). FIG. 6B shows the tube 52 after it has expanded enough to reach the inner circular wall 54 of the mold cavity. Once the polymer material has reached the walls 54 of the cavity 50 the internal pressure may be increased or maintained to force the polymer material into the pleat-forming slots 55. FIG. 6C illustrates the balloon shape formed by the mold after material has filled the slots 55. The pressure is then relieved and the temperature lowered quickly to anneal the material so that the balloon takes its final form.

The pleats are then preferably wrapped in a spiral fashion around the hub portion of the balloon (see FIG. 5A). This wrapping step is performed after the balloon ends are sealed to the catheter shaft. After wrapping the pleats about the catheter shaft, the balloon is placed within a sheath and the temperature elevated to heat set the pleats in place. The wrapping step may be performed by hand or using a wrapping machine as described in US2005/0244533.

Figure 4A:
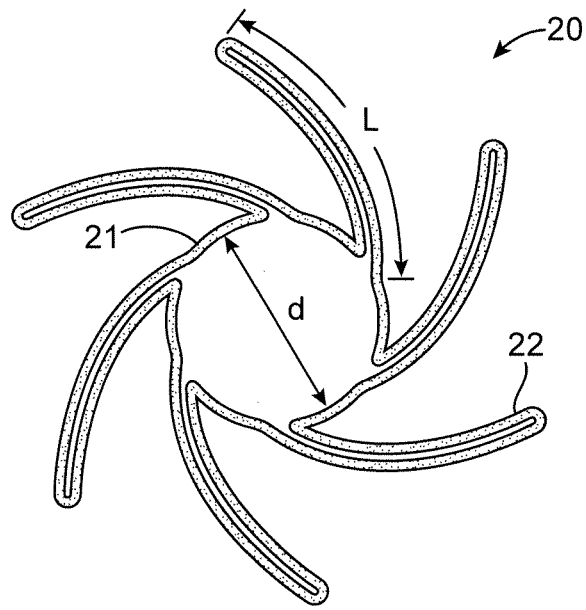
FIG. 4A shows a cross-sectional view of a six-pleated balloon. The pleats are shown partially wrapped around a hub of the balloon in spiral fashion.
Figure 4B:
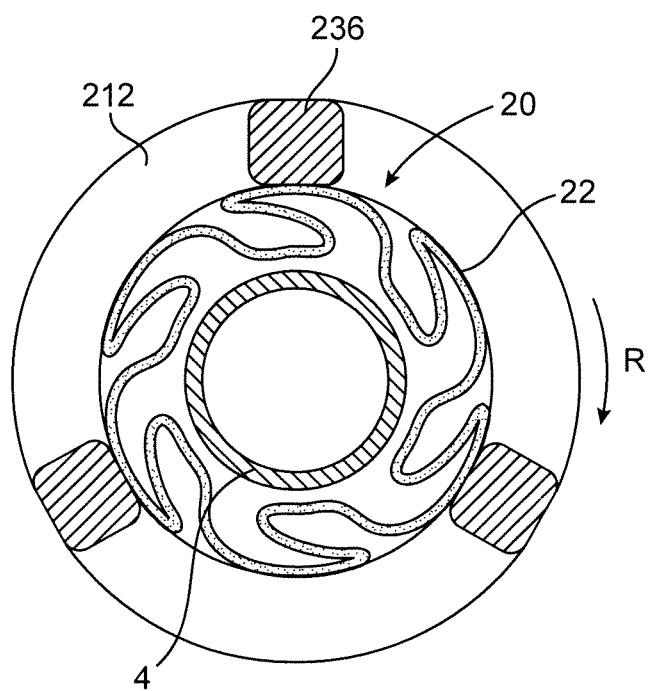
FIG. 4B shows a cross-sectional view of a scaffold partially crimped to the six-pleated balloon of FIG. 5A with the balloon partially inflated and pleats partially opened.
Figure 7A:
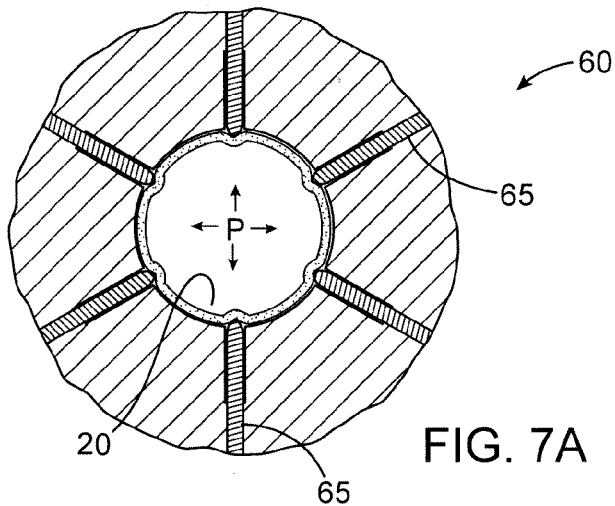
FIGS. 7A-7C illustrate an alternative process for making a multi-pleated balloon. Shown is a forming chamber for forming pleats in a balloon using radially extending fingers.
Figure 7B:
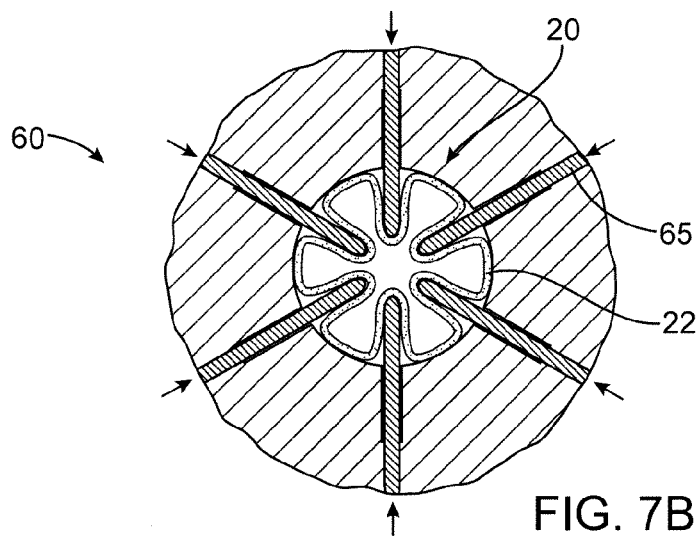
Figure 7C:
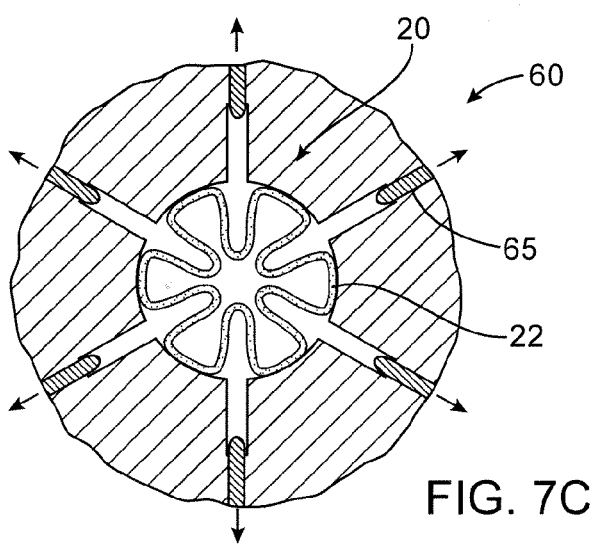

As an alternative to the process described in FIGS. 6A-6C, the multi-pleated balloon 20/30 may be formed by a two-step process. The extruded tube is first radially expanded in a circular tube having an inner wall corresponding to the expanded balloon diameter. The balloon is then annealed. Next, the balloon is placed in a forming chamber 60 to form pleats. Referring to FIGS. 7A-7C, the chamber has openings 62 to provide passage of inwardly extendible pleat-forming fingers 65 into the interior of the chamber 60. The balloon 20 is lightly inflated. The fingers 65 are then extended into the chamber 60 interior to form the pleats 22. FIG. 7B shows the fingers 65 when fully extended into the chamber 60 and FIG. 7C shows the balloon shape (with 6 pleats formed) after the fingers 65 are withdrawn from the chamber 60. The fingers 65 are suitably rounded at the tips (so as to not weaken the balloon material when being pushed inwardly) and configured to extend down to a diameter corresponding to the outer diameter of the balloon hub 21 (FIG. 4A). The balloon 20 may be warmed to, e.g., about 60 deg Celsius for a PEBAX balloon, when the fingers 65 are extended into the balloon 20, or the balloon 20 may be kept at room temperature so as to cold-form the pleats 22 using the fingers 65. The forming chamber 60 is shown for a 6 pleated balloon, but may be alternatively configured to make a 6, 9, 12 or 15 pleated balloon.

Referring to FIG. 4A, the inner diameter D of the formed balloon 20 is selected, in part, based on the outer diameter of the catheter shaft where the balloon will be attached. The diameter D should be selected so that fluid supplied to the balloon through the catheter lumen has a sufficiently sized passageway to inflate the balloon without causing excessive stress on the ends of the polymer material sealed to the catheter shaft at the balloon ends, or otherwise causing failure in the balloon when the balloon is inflated to the maximum desired safe operating pressure. The length L of the pleats is selected, in part, based on the desired maximum expanded diameter. For a given inner diameter D and desired outer diameter for the expanded balloon, the length of pleats decreases with an increasing number of pleats.

As an alternative to the process described in FIGS. 7A-7C, the balloon may be both radially expanded from the extruded tube and formed with pleats within the same chamber or cavity.

Preferred Scaffold Pattern

As noted above, in a preferred embodiment a scaffold has the pattern described in U.S. application Ser. No. 12/447,758 (US 2010/0004735) to Yang & Jow, et al. Other examples of scaffold patterns suitable for PLLA are found in US 2008/0275537. FIG. 3 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 3 for clarity. In FIG. 3, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 3, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 in the intermediate portion 216 of the strut pattern 200. The distances 242 are the same or substantially the same for each link strut 234 in the intermediate portion 216. The ring struts 230 have widths 237 that are uniform in dimension along the individual lengthwise axis 213 of the ring strut. The ring strut widths 234 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 3, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236 of the intermediate portion 216. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236 in the intermediate portion 216.

It will be appreciated from FIG. 3 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 232 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method for making a medical device, comprising the steps of:
    providing a polymer scaffold having a longitudinal axis, pre-crimp diameter and a pair of ring elements connected to each other by at least two linking elements;
    placing the scaffold having the pre-crimp diameter over a balloon having at least six pleats to increase a uniformity of expansion of the scaffold; and
    crimping the scaffold to the balloon, including:
        placing the scaffold and balloon in a crimping mechanism,
        reducing the scaffold diameter from the pre-crimp diameter to a first diameter,
    wherein the balloon is not inflated prior to the scaffold diameter being reduced to the first diameter,
        maintaining the scaffold at the first diameter for a dwell period, and
        reducing the scaffold diameter to a final crimp diameter that is less than the first diameter.

2. The method of claim 1, wherein the balloon has 9, 12 or 15 pleats, or between 9 and 15 pleats.

3. The method of claim 1, wherein the pre-crimp diameter is at least twice the final crimp diameter.

4. The method of claim 1, wherein the balloon is inflated after the scaffold diameter is reduced to the first diameter.

5. The method of claim 4, wherein the first diameter is 50% or less than 50% of the pre-crimp diameter.

6. The method of claim 1, wherein the balloon is inflated after the scaffold has the first diameter, and wherein the first diameter is such that the pleats of the inflated balloon only partially open so that the pleats are maintained as the scaffold is crimped to the final crimp diameter.

7. The method of claim 6, wherein the balloon is inflated to about 20-80% of a nominal balloon inflation pressure, or about 10-30% of an over-inflated or maximum balloon inflation pressure.

8. The method of claim 1, wherein the scaffold is crimped to a balloon having an inflated diameter that is about 2.5 times higher than the final crimp diameter.

9. The method of claim 1, wherein the scaffold is made from PLLA, the crimping step further including the step of increasing the retention force between the scaffold and balloon including maintaining a scaffold temperature between 40 and 55 degrees Celsius during crimping.

10. The method of claim 1, wherein after the scaffold has the first diameter the scaffold is removed from the crimping mechanism, an alignment of the scaffold with respect to balloon markers is verified, and the scaffold is returned to the crimping mechanism.

11. A method for making a medical device, comprising the steps of:
    providing a polymer scaffold having a pre-crimp diameter and a pair of ring elements connected to each other by N linking elements, wherein N is greater than or equal to 2;
    placing the scaffold having the pre-crimp diameter over a balloon having at least 2N pleats; and
    crimping the scaffold to the balloon, including:
        reducing the scaffold diameter from the pre-crimp diameter to a first diameter,
    wherein the balloon pleats cannot fully open when the scaffold has a diameter equal to or less than the first diameter,
        inflating the balloon not until the scaffold diameter is reduced to the first diameter, and
        reducing the scaffold diameter from the first diameter to a final crimp diameter.

12. The method of claim 11, wherein N is equal to 2 or 3.

13. The method of claim 11, wherein there are three pleats for every linking element.

14. The method of claim 11, wherein the scaffold is crimped to the first diameter using a crimping mechanism, and wherein after the scaffold has the first diameter the scaffold is removed from the crimping mechanism, an alignment of the scaffold with respect to balloon markers is verified, and the scaffold is returned to the crimping mechanism.

15. A method for making a medical device, comprising the steps of:
    providing a polymer scaffold made from PLLA and having a pre-crimp diameter;
    crimping the scaffold to a balloon so as to both increase a uniformity of expansion when the scaffold is expanded by the balloon and increase a retention force between the crimped scaffold and balloon, including the steps of
        crimping the scaffold to a balloon having at least six pleats, and
        crimping while the scaffold has an elevated temperature of between 40 and 55 degrees Celsius,
    wherein the balloon has the at least six pleats before the scaffold is crimped to the balloon, and
    wherein the crimping step further includes inflating the balloon only after the scaffold attains a first diameter that is 50% or less than 50% of the pre-crimp diameter.

16. The method of claim 15, wherein the scaffold has a network of interconnected structure including a pair of ring elements connected to each other by linking elements, wherein the pair of rings and linking elements from a plurality of cells, and wherein there are at least three pleats for every cell.

17. The method of claim 15, wherein the scaffold is crimped to the first diameter using a crimping mechanism, and wherein after the scaffold has the first diameter the scaffold is removed from the crimping mechanism, an alignment of the scaffold with respect to balloon markers is verified, and the scaffold is returned to the crimping mechanism.

* * * * *